(12) United States Patent
Levine

(10) Patent No.: US 7,288,110 B1
(45) Date of Patent: Oct. 30, 2007

(54) HEATER DEVICE FOR HEATING A USER'S HANDS AND FEET

(76) Inventor: Stacey M. Levine, 615 Broadway, Unit 48, Amityville, NY (US) 11701

(*) Notice: Subject to any disclaimer, the term of this patent is extended or adjusted under 35 U.S.C. 154(b) by 337 days.

(21) Appl. No.: 11/136,904

(22) Filed: May 26, 2005

(51) Int. Cl.
*A61F 7/00* (2006.01)
(52) U.S. Cl. ...................... 607/108; 607/104
(58) Field of Classification Search ............. 607/104, 607/108–112, 114
See application file for complete search history.

(56) References Cited

U.S. PATENT DOCUMENTS

| | | | |
|---|---|---|---|
| 1,558,278 A | 10/1925 | Phillips | |
| 4,495,935 A | 1/1985 | Lanier | |
| 5,088,549 A | 2/1992 | Schneider | |
| 5,456,704 A | 10/1995 | Kilcullen | |
| 6,185,845 B1 | 2/2001 | Gordon | |
| 6,701,639 B2 | 3/2004 | Treptow et al. | |

*Primary Examiner*—Henry M. Johnson, III
*Assistant Examiner*—Aaron Roane
(74) *Attorney, Agent, or Firm*—Donald R. Schoonover

(57) ABSTRACT

A heater device includes a pad that is heated by electrically heated fluid and which has areas for a user to insert his or her feet and areas for a user to insert his or her hands whereby either or both the user's feet and/or hands can be heated in an efficient manner.

1 Claim, 1 Drawing Sheet

HEATER DEVICE FOR HEATING A USER'S HANDS AND FEET

BACKGROUND OF THE INVENTION

1. Field of the Invention

The present invention relates to the general art of footwear, and to the particular field of protective footwear.

2. Description of the Related Art

In recent years, a great many people are engaging in outdoor sports such as skiing as well as many outdoor activities, including working. Those who engage in these activities are often exposed to the elements for extended periods of time. Such exposure can lead to discomfort or, more seriously, to frost bite particularly in the extremities. It is therefore vital that people who may spend a great deal of time outdoors seek protection from the elements in order to prevent the occurrence of exposure and frost bite.

The cooling of the extremities, has long been recognized as a serious deterrent to performing activities in cold temperatures and various proposals have been advanced for dealing with this problem. In the case of feet, most footwear known to the inventor, which has been designed for use in cold weather, has utilized hard and heavy materials on the sole and sometimes on the uppers as well. For instance, hard rubber soles are most commonly used for winter boots and overboots. Since such footwear is generally constructed with rigid sole structures, carrying and storing the footwear can be difficult.

Also, other footwear known to the inventor, designed for use in cold weather, has utilized conventional insulating materials, such as goose down, stiff insulating foam or synthetic fibers, to reduce the loss of heat from the wearer's foot. While these insulating materials attempt to minimize the heat loss from the wearer's foot, all of these insulating materials have various drawbacks.

A foot cover that is easy to manufacture, is easy to use, is lightweight, is easy to carry, is easy to store, is washable, and is highly effective at keeping the wearer's feet warm would be of considerable value.

A variety of other devices and methods are known for this purpose. For example, footwear can be provided with insulation or made waterproof. Such methods have significant drawbacks. For example, waterproofing methods provide no manner of either retaining heat or providing additional heat to the wearer's feet. Rather, they only prevent the introduction of water or other liquid, which could make the wearer's feet cold. Insulation is largely ineffective as well because it merely retains body heat without providing any additional heat.

One method of providing a heat source in footwear involves placing an electric heating element in the shoe or boot liner and using a battery to supply energy to the heating element. Another attempt to solve the problem of cold feet has involved the use of electrical heating elements in socks. Foot warming devices that use electric heating elements have a number of disadvantages. First and foremost, they can be dangerous. Specifically, they can create the risk of electric shock, sparks that could cause flammable socks and/or footwear materials to catch fire which in turn could burn the wearer's feet, and electrical shortages. Such electrical devices can also be expensive and inconvenient to use.

It is also known to adapt the insoles of boots, shoes and the like to accommodate a heat dispensing material in a pocket formed in the insole. These devices also have significant disadvantages. Specifically, they contemplate permanently modifying the footwear itself to accommodate the heat dispensing material. This could permanently add weight and bulk to the footwear which is unnecessary, especially when the footwear is worn in warm environments. In addition, these devices do not allow for adequate circulation of the generated heat to the wearer's feet.

Some prior art foot warmers include a removable insole for footwear that has a reduced thickness portion in the padding layer creating a cavity for holding a heat source that produces heat from an exothermic chemical reaction. These insoles often have an upper layer that has a plurality of holes for facilitating heat transfer from the heat source to the wearer.

Although an improvement, these insoles also have significant drawbacks. First and foremost, the heat source is generally enclosed in the cavity in such a way that the amount of air that can reach the heat source is limited. Thus, because the heat source needs oxygen to drive the chemical reaction necessary to generate heat, the amount of heat produced is greatly inhibited. The heat source is also enclosed in the cavity in such a way that the heat generated by the heat source cannot adequately circulate so that the wearer's feet are not effectively heated.

Still further, while a person's feet have received much attention in the above-described situations, a user's hands also may suffer the same problems when exposed to cold temperatures. While the inventor is aware of several devices that are intended to keep a user's hands warm, including gloves, mittens, heated gloves and mittens, the inventor is not aware of any device that can be used for either or both a user's feet and/or hands. Accordingly, a user is required to carry items for his or her hands as well as additional items for his or her feet. This can be cumbersome and inconvenient.

Therefore, there is a need for a device that can be used to heat a user's feet and/or hands.

PRINCIPAL OBJECTS OF THE INVENTION

It is a main object of the present invention to provide a device for efficiently heating a user's feet and hands.

It is another object of the present invention to provide a device which can efficiently heat both a user's feet and hands.

It is another object of the present invention to provide a device for heating a user's feet and hands and is convenient and easy to use.

SUMMARY OF THE INVENTION

These, and other, objects are achieved by a heater device that includes formed areas for both feet and hands whereby a user can insert his or her feet or hands to be warmed. The device includes a pad that is heated by coils that are electrically heated and transfer the electric heat to a fluid and transfer the heat from the fluid to the pad.

Using the heater device embodying the present invention will permit a user to heat his or her hands and/or feet as needed. The device is convenient, safe and efficient.

BRIEF DESCRIPTION OF THE DRAWING FIGURES

DETAILED DESCRIPTION OF THE PREFERRED EMBODIMENT

Figure 1:
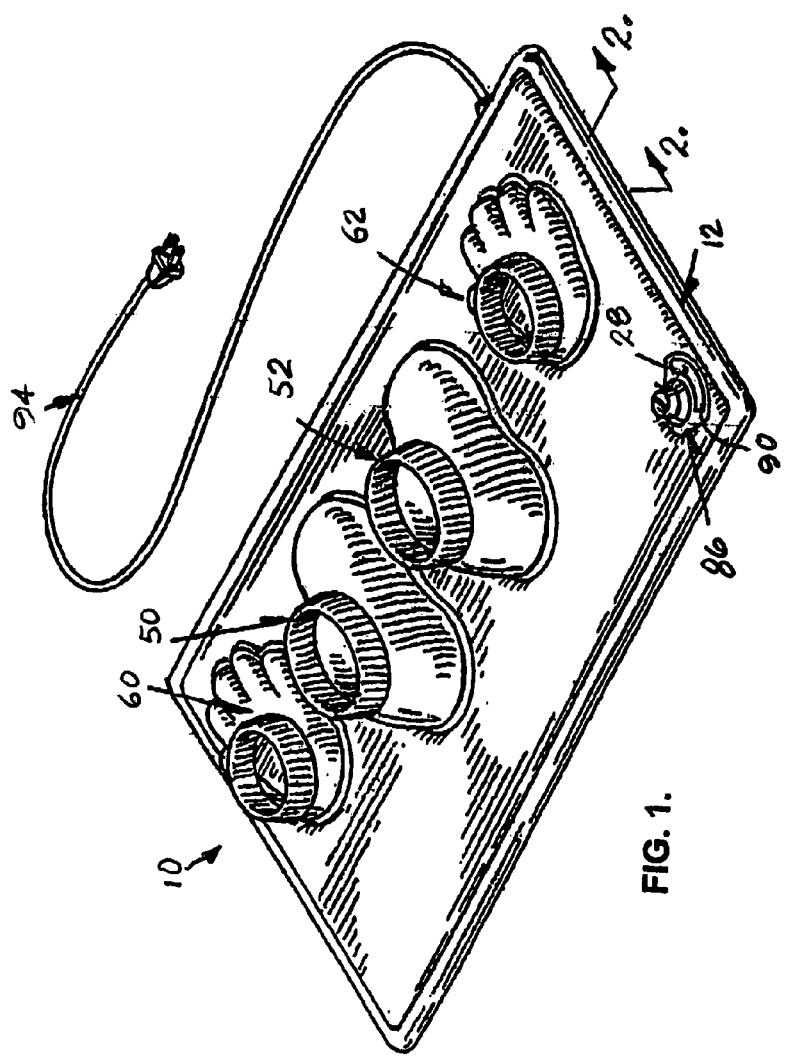
FIG. 1 is a perspective view of a hand and foot heater device embodying the present invention in a use condition.
Figure 2:
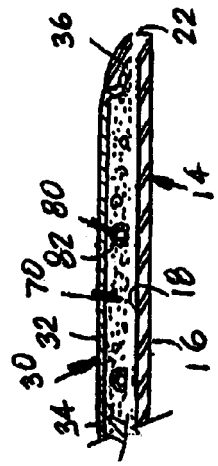
FIG. 2 is an elevational view taken along line 2-2 of FIG. 1.

Other objects, features and advantages of the invention will become apparent from a consideration of the following detailed description and the accompanying drawings.

Referring to the Figures, it can be understood that the present invention is embodied in a hand and foot heater device 10 that achieves the above-stated objectives.

Device 10 comprises a base pad 12 which includes a first layer 14 that is a bottom layer when base pad 12 is in use. First layer 14 has a first surface 16, that is an outer surface when base pad 12 is in use, and a second surface 18, that is an inner surface when base pad 12 is in use. First layer 14 further includes and a peripheral edge 22. First layer 14 can be rubber-like material to prevent slipping if desired.

Base pad 12 further includes a second layer 30 that is a top layer when base pad i12 is in use. Second layer 30 has a first surface 32, that is an outer surface when base pad 12 is in use, and a second surface 34, that is an inner surface when base pad 12 is in use. Second layer 30 further includes a peripheral edge 36.

Peripheral edge 22 of the first layer 14 is connected to peripheral edge 36 of the second layer 30.

Inner surface 18 of the first layer 14 is spaced apart from inner surface 34 of the second layer 30 and an interior volume 40 is defined between the inner surface 18 of the first layer 14 and the inner surface 34 of the second layer 30.

Two shoe-shaped shoe-accommodating units 50 and 52 are located on second layer 30 to be located on first surface 32 of the second layer 30. Two hand-shaped hand-accommodating units 60 and 62 are located on first surface 32 of the second layer 30. Hand-shaped hand-accommodating units 60 and 62 are located adjacent to shoe-shaped shoe-accommodating units 50 and 52.

A layer of insulation 70 is located in interior volume 40.

A plurality of fluid-containing coils, such as coil 80, are located in interior volume 40. Fluid, such as oil or the like is contained in the coils.

An electrical heating coil, such as heating coil 82, is wrapped around each fluid-containing coil 80 to be in heat transferring relationship therewith.

A switch 86 is located on second layer 30 of base pad 12 and has an "on" position 88 and an "off" position 90 and can be a rheostat-type switch so various levels of power can be transferred through the switch 86 according to the setting of the switch 86. Switch 86 is electrically connected to each heating coil 82. Switch 86 is of the type known to those skilled in the circuitry art and since the exact details of the electric circuit associated with device 10 are not important to the present invention, such details will not be discussed in detail.

A power cord 94 is electrically connected to switch 86 to transfer electric power from a source (not shown) to each heating coil 82 to activate each heating coil 82 when the switch 86 is in the "on" position 88. Each heating coil 82 generates heat when activated with the heat generated being transferred to the fluid-containing coil 80 associated therewith and heating fluid contained in the associated fluid-containing coil 80.

Each fluid-containing coil 80 is in heat transferring relationship with the hand-shaped hand-accommodating units 60, 62 and the shoe-shaped shoe-accommodating units 50, 52 to transfer heat thereto when desired.

Operation of device 10 can be understood from the teaching of the foregoing disclosure and thus will not be presented in detail. If a user desires to warm his or her hands, he or she places his or her hands into the hand-shaped hand-accommodating units 60, 62 after activating switch 86. If a user desires to warm his or her feet, he or she places his or her feet into the shoe-shaped shoe-accommodating units 50, 52 after activating the switch 86. The user's hands and feet can be warmed at the same time if desired.

It is understood that while certain forms of the present invention have been illustrated and described herein, it is not to be limited to the specific forms or arrangements of parts described and shown.

What is claimed and desired to be covered by Letters Patent is:

1. A hand and foot heater device comprising:
    (a) a base pad which includes
        (1) a first layer that is a bottom layer when said base pad is in use, the first layer having a first surface that is an outer surface when said base pad is in use, a second surface that is an inner surface when said base pad is in use, and a peripheral edge,
        (2) a second layer that is a top layer when said base pad is in use, the second layer having a first surface that is an outer surface when said base pad is in use, a second surface that is an inner surface when said base pad is in use, and a peripheral edge,
        (3) the peripheral edge of the first layer being connected to the peripheral edge of the second layer, and
        (4) the inner surface of the first layer being spaced apart from the inner surface of the second layer and defining an interior volume between the inner surface of the first layer and the inner surface of the second layer;
    (b) two shoe-shaped shoe-accommodating units located on the second layer to be located on the first surface of the second layer;
    (c) two hand-shaped hand-accommodating units located on the second layer to be located on the first surface of the second layer, said hand-shaped hand-accommodating units being located adjacent to the shoe-shaped shoe-accommodating units;
    (d) a layer of insulation located in the interior volume;
    (e) a plurality of fluid-containing coils located in the interior volume;
    (f) an electrical heating coil wrapped around each fluid-containing coil to be in heat transferring relationship therewith;
    (g) a switch on the second layer of said base pad and having an "on" position and an "off" position, said switch being electrically connected to each heating coil;
    (h) a power cord electrically connected to said switch to transfer electric power from a source to each heating coil to activate each heating coil when said switch is in the "on" position, each heating coil generating heat when activated with the heat generated being transferred to the fluid-containing coil associated therewith and heating fluid contained in the associated fluid-containing coil; and
    (i) each fluid-containing coil being in heat transferring relationship with said hand-shaped hand-accommodating units and said shoe-shaped shoe-accommodating units.

\* \* \* \* \*